US006561975B1

(12) United States Patent
Pool et al.

(10) Patent No.: US 6,561,975 B1
(45) Date of Patent: May 13, 2003

(54) METHOD AND APPARATUS FOR COMMUNICATING WITH MEDICAL DEVICE SYSTEMS

(75) Inventors: Nancy Perry Pool, Minnetonka, MN (US); Mary Wesolowski Leadholm, St. Paul, MN (US)

(73) Assignee: MedTronic, Inc., Minneapolis, MN (US)

( * ) Notice: Subject to any disclaimer, the term of this patent is extended or adjusted under 35 U.S.C. 154(b) by 110 days.

(21) Appl. No.: 09/696,319

(22) Filed: Oct. 25, 2000

Related U.S. Application Data
(60) Provisional application No. 60/197,753, filed on Apr. 19, 2000.

(51) Int. Cl.⁷ .................................................. A61B 5/00
(52) U.S. Cl. ........................... 600/300; 607/60; 607/32; 607/5; 607/9; 607/63
(58) Field of Search ................................. 600/300, 517, 600/515, 508, 509, 523, 437; 128/903; 607/60, 32, 30, 2, 3, 4, 5, 9, 25, 62, 63

(56) References Cited

U.S. PATENT DOCUMENTS

| 4,494,950 | A | * | 1/1985 | Fischell ....................... 604/66 |
| 4,928,690 | A | * | 5/1990 | Heilman et al. ............... 607/4 |
| 5,078,134 | A | * | 1/1992 | Heilman et al. ............... 607/4 |
| 5,853,005 | A | * | 12/1998 | Scanlon ....................... 600/437 |
| 6,115,636 | A | | 9/2000 | Ryan ........................... 607/60 |
| 6,272,379 | B1 | * | 8/2001 | Fischell et al. ................ 607/5 |
| 6,409,675 | B1 | * | 6/2002 | Turcott ....................... 600/508 |

FOREIGN PATENT DOCUMENTS

| WO | 9611722 | 4/1996 | ............ A61N/1/36 |
| WO | 9700708 | 1/1997 | .......... A61N/1/372 |
| WO | 0006018 | 2/2000 | ............ A61B/5/02 |

OTHER PUBLICATIONS

09/356,340, Koen J. Weijand, "A Medical System having Improved Telemetry" Filed Jul. 19, 1999.
09/358,081, Krichen et al., "A System and Method for Transferring Information Relating to an Implantable Medical Device to a Remote Location" Filed Jul. 21, 1999.
09/426,741, Kurt R. Linberg, "Apparatus and Method for Remote Troubleshooting, Maintenance and Upgrade of Implantable Device Systems" Filed Oct. 26, 1999.
09/429,956, Kurt R. Linberg, "Apparatus and Method for Remote Self–Identification of Components in Medical Device Systems" Filed Oct. 29, 1999.
09/429,960, Nichols et al., "Apparatus and Method to Automate Remote Softward Updates of Medical Device Systems" Filed Oct. 29, 1999.
09/430,208, Kurt R. Linberg, "Apparatus and Method for Automated Invoicing of Medical Device Systems" Filed Oct. 29, 1999.

(List continued on next page.)

Primary Examiner—Teresa Walberg
Assistant Examiner—Fadi H. Dahbour
(74) Attorney, Agent, or Firm—Girma Wolde-Michael

(57) ABSTRACT

A wearable telemetry arrangement is used with a medical information communications device in a telemetry system for communicating with an implantable medical device. In an example embodiment, the telemetry arrangement includes an article configured and arranged to be physically coupled to and donned on a body. In addition, an antenna member is located on the article that is configured and arranged to establish a communications link between the implanted device and the medical communications system. The telemetry arrangement of the present invention provides a reliable and non-invasive system that conveniently and chronically collects cardiac and other implanted medical device data. Further, the system is adaptable to patient management modules and portals to provide remote connectivity to web-based platforms and data management systems.

44 Claims, 3 Drawing Sheets

OTHER PUBLICATIONS

09/430,708, Michael E. Behm, "Tactile Feedback for Indicating Validity of Communication Link With an Implantable Medical Device" Filed Oct. 29, 1999.

09/431,881, Timothy Joseph Nichols, "Method and Apparatus to Secure Data Transfer from Medical Device Systems" Filed Nov. 2, 1999.

09/433,477, Thomas J. Winkler, "Implantable Medical Device Programming Apparatus Having an Auxiliary Component Storage Compartment" Filed Nov. 4, 1999.

09/437,615, Kurt R. Linberg, "Remote Delivery of Software–Based Training for Implantable Medical Device Systems" Filed Nov. 10, 1999.

09/460,580, Nelson et al., "Apparatus and Method for Remote Therapy and Diagnosis in Medical Devices Via Interface Systems" Filed Dec. 14, 1999.

09/466,284, Linberg et al., "Virtual Remote Monitor, Alert, Diagnostics and Programming for Implantable Medical Device Systems" Filed Dec. 17, 1999.

09/474,694, Kurt R. Linberg, "System of Notification of Recalled Components for a Medical Device" Filed Dec. 29, 1999.

09/475,709, Warkentin et al., "A Communications System for an Implantable Device and a Drug Dispenser" Filed Dec. 30, 1999.

60/172,937, Ferek–Petric et al., "Instrument and Software for Remote Monitoring and Programming ofImplantable Medical Devices (IMDs)" Filed Dec. 12, 1999.

60/173,062, Riff et al., "Chronic Real–Time Information Management Systems for Implantable Medical Devices (IMDs)" Filed Dec. 23, 1999.

60/173,064, Stomberg et al., An Information Network Scheme for Interrogation of Implantable Medical Devices (IMDs) Filed Dec. 23, 1999.

60/173,065, Bozidar Ferek–Petric, "Medical Device GUI for Cardiac Electrophysiology Display and Data Communications" Filed Dec. 23, 1999.

60/173,071, Goedeke et al., "Automatic Voice and Data Recognition for Medical Device Instrument Systems" Filed Dec. 23, 1999.

60/173,079, Lee et al., "Large–Scale Processing Loop for Implantable Medical Devices (IMDs)" Filed Dec. 23, 1999.

60/173,080, Michael Thomas Lee, "Central Switchboard to Facilitate Remote Collaboration with Medical Instruments" Filed Dec. 23, 1999.

60/173,081, Stomberg et al., "Application Proxy for Telecommunication–Enabled Remote Medical Device Access Instruments" Filed Dec. 23, 1999.

60/173,082, Merry et al., "Integrated Software System for Implantable Medical Device Installation and Management" Filed Dec. 23, 1999.

60/173,083, Nelson et al., "Dynamic Bandwidth Monitor and Adjuster for Remote Communications With a Medical Device" Filed Dec. 23, 1999.

60/173,822, Nichols et al., "User Authentication in Medical Device Systems" Filed Dec. 30, 1999.

60/180,285, Christopherson et al., "Information Remote Monitor (IRM) Medical Device" Filed Feb. 4, 2000.

60/180,289, McMenimen, et al., "Responsive Manufacturing Inventory Control" Filed Feb. 4, 2000.

60/184,221, Goedeke et al., "Follow–Up Monitor for Implantable Medical Device" Filed Feb. 23, 2000.

60/186,235, Cao, et al., "An Implantable Medical Device With Multi–Vector Sensing Electrodes" Filed Feb. 29. 2000.

60/187,280, Donovan et al., "Stimulator for Delivery of Molecular Therapy" Filed Mar. 6, 2000.

60/189,562, Linberg et al., Individualized, Integrated, and Informative Internet Portal for Holistic Management of Patients with Implantable Devices, Filed Mar. 15, 2000.

60/190,272, Webb et al., "Heart Failure Monitor Quick Look Summary for Patient Management Systems" Filed Mar. 16, 2000.

60/190,465, Taepke et al., "A Universal Interface for Medical Device Data Management" Filed Mar. 17, 2000.

60/192,006, James D. Webb, "Telepresence Apparatus and Method for Remote Implantable Medical Device Implementation and Management" Filed Mar. 24, 2000.

60/192,943, Au et al., "A Hand–Held Surface ECG and RF Apparatus Incorporated With a Medical Device" Filed Mar. 29, 2000.

60/193,881, David L. Thompson, Variable Encryption Scheme for Data Transfer Between Medical Devicds and Related Data Management Systems Filed Mar. 31, 2000.

60/194,512, Goedeke et al., "Implantable Medical Device Controlled by a Non–Invasive Physiological Data Measurement Device" Filed Apr. 4, 2000.

* cited by examiner

METHOD AND APPARATUS FOR COMMUNICATING WITH MEDICAL DEVICE SYSTEMS

RELATED PATENT DOCUMENTS

This application claims priority to and is a conversion of U.S. Provisional Application Ser. No. 60/197,753, filed on Apr. 19, 2000, entitled "ECG and RF Apparatus For Medical Device Systems", which is incorporated herein by reference in it's entirety. The current application relates to, and incorporates common subject matter therein, U.S. Ser. No. 09/218,946, now U.S. Pat. No. 6,115,636 to Ryan. The present invention is adaptable to remote patient management and chronic systems as illustrated and described in applications assigned to the assignee of record entitled "System and Method for Transferring Information Relating to an Implantable Medical Device to a Remote Location," filed on Jul. 21, 1999, Ser. No. 09/358,081, now U.S. Pat. No. 6,250,309; "Apparatus and Method for Remote Troubleshooting, Maintenance and Upgrade of Implantable Device Systems," filed on Oct. 26, 1999, Ser. No. 09/426,741, now U.S. Pat. No. 6,442,433; "Tactile Feedback for Indicating Validity of Communication Link with an Implantable Medical Device," filed Oct. 29, 1999, Ser. No. 09/430,708; "Apparatus and Method for Automated Invoicing of Medical Device Systems," filed on Oct. 29, 1999, Ser. No. 09/430,208, now U.S. Pat. No. 6,385,593; "Apparatus and Method for Remote Self-Identification of Components in Medical Device Systems," filed Oct. 29, 1999, Ser. No. 09/429,956, now abandoned in favor of continuation application Ser. No. 10/010,406, filed Dec. 7,2001; "Apparatus and Method to Automate Remote Software Updates of Medical Device Systems," filed Oct. 29, 1999, Ser. No. 09/429,960, now U.S. Pat. No. 6,363,282; "Method and Apparatus to Secure Data Transfer From Medical Device Systems," filed Nov. 2, 1999, Ser. No. 09/431,881; "Implantable Medical Device Programming Apparatus Having an Auxiliary Component Storage Compartment," filed Nov. 4, 1999, Ser. No. 09/433, 477, now U.S. Pat. No. 6,411,851; "Remote Delivery of Software-Based Training for Implantable Medical Device Systems," filed Nov. 10, 1999, Ser. No. 09/437,615, now U.S. Pat. No. 6,386,882; "Medical System Having Improved Telemetry," filed Jul. 19, 1999, Ser. No. 09/356,340, now U.S. Pat. No. 6,298,271; "Apparatus and Method for Remote Therapy and Diagnosis in Medical Devices Via Interface Systems," filed Dec. 14, 1999, Ser. No. 09/460, 580, now U.S. Pat. No. 6,418,346; "Virtual Remote Monitor, Alert, Diagnostics and Programming for Implantable Medical Device Systems" filed Dec. 17, 1999, Ser. No. 09/466, 284, now U.S. Pat. No. 6,497,655; "System of Notification of Recalled Components for a Medical Device," filed Dec. 29, 1999, Ser. No. 09/474,694; "A Communications System for an Implantable Device and a Drug Dispenser," filed Dec. 30, 1999, Ser. No. 09/475,709, now U.S. Pat. No. 6,471,645; "Instrumentation and Software for Remote Monitoring and Programming of Implantable Medical Devices (IMDs)," filed Dec. 20, 1999, Ser. No. 09/745,112; "An information Network Scheme for Interrogation of Implantable Medical Devices (IMDs)," filed Dec. 18, 2000, Ser. No. 09/740,128, now U.S. Pat. No. 6,480,745; "Medical Device GUI for Cardiac Electrophysiology Display and Data Communications," filed Dec. 21, 2000, Ser. No. 09/746,230, now U.S. Pat. No. 6,473,638; Integrated Software System for Implantable Medical Device Installation and Management," filed Dec. 18, 2000, Ser. No. 09/740,078; "Dynamic Bandwidth Monitor and Adjuster for Remote Communications with a Medical Device," filed Dec. 20, 2000, Ser. No. 09/745,143; "Large-Scale Processing Loop for Implantable Medical Devices (IMDs)," filed Dec. 18, 2000, Ser. No. 09/740,080; "A Method and System for Using Implanted Medical Device Data for Accessing Therapies," filed Dec. 18, 2000, Ser. No. 09/740,127; "Automatic Voice and Data Recognition for Medical Device Instrument Systems," filed Dec. 6, 2000, Ser. No. 09/731, 178; "Central Switchboard to Facilitate Remote Collaboration with Medical Instruments," filed Dec. 20, 2000, Ser. No. 09/745,038, now U.S. Pat. No. 6,442,432; "Method and a System for Conducting Failure Mode Recovery in an Implanted Medical Device," filed Dec. 6, 2000, Ser. No. 09/731,222; "User Authentication in Medical Systems Device," filed Dec. 29, 2000, Ser. No. 09/750,739; "Apparatus and Method for Automated Invoicing of Medical Device Systems," filed Oct. 29, 1999, Ser. No. 60/173,824, now abandoned; "Responsive Manufacturing and Inventory Control," filed Feb. 1, 2001, Ser. No. 09/775,281; "Information Remote Monitor (IRM) Medical Device," filed Feb. 2, 2001, Ser. No. 09/776,265; "Follow-up Monitoring Method and System for Implantable Medical Device," filed Dec. 8, 2000, Ser. No. 09/732,951; "An Implantable Medical Device with Multi-Vector Sensing Electrodes," filed Mar. 1, 2001, Ser. No. 09/797,031; "Stimulator for Delivery of Molecular Therapy," filed Mar. 5, 2001, Ser. No. 09/799, 304; "Individualized, Integrated and Informative Internet Portal for Holistic Management of Patients with Implantable Devices," filed Mar. 15, 2001, Ser. No. 09/809,483; "Heart Failure Monitor Quick-Look Summary for Patient Management Systems," filed Mar. 16, 2001, Ser. No. 09/809,915; "A Universal Interface for Medical Device Data Management," filed Mar. 16, 2001, Ser. No. 09/809,914; "System and Method for Providing Remote Expert Communication and Video Capabilities for Use During Medical Procedure," filed filed Mar. 24, 2000, Ser. No. 09/815,728; "A Hand-Held Surface ECG and RF Apparatus Incorporated with a Medical Device," filed Mar. 29, 2001, Ser. No. 09/821,201; "Variable Encryption Scheme for Data Transfer Between Medical Devices and Related Data Management Systems," filed Mar. 30, 2000, Ser. No. 09/821,518; "Implantable Medical Device Controlled by a Non-Invasive Physiological Data Measurement Device," filed Apr. 4, 2001, Ser. No. 09/825, 909, which are, in relevant parts, all incorporated by reference herein.

FIELD OF THE INVENTION

The present invention generally relates to communicating via telemetry with implantable medical devices and instruments. Specifically, the invention relates to a method and an apparatus for enabling the sensing of outputs, and/or real time communication with, various medical devices for chronic patient management.

BACKGROUND OF THE INVENTION

In recent years, implantable electronic device technology has rapidly advanced. Sizes and weights of implantable devices have decreased; while functionality has increased. These advances have created a corresponding demand for two-way communication or telemetry between the implantable electronic device and an external device, (e.g. a programmer). In a pacemaker system, a programmer downloads to an implanted pacemaker, data such as operating parameters. Likewise, data may flow in the opposite direction; that is, from the implantable device to the programmer for analysis. In fact, modem pacemakers are capable of storing significant amounts of data about the patient (e.g., average heart rate) and the pacemaker itself (e.g. battery voltage), which may need to be frequently transmitted to the programmer for, evaluation by the physician.

A programmer used during a telemetry procedure is typically positioned remotely from the patient's implanted device. A programming head of the programmer unit, e.g., a wand or some other extendible head, containing at least an antenna, is connected to the remainder of the programmer unit via a stretchable coil cable and is positioned over the patient's implanted device site for programming or telemetry interrogation of the implanted device. The programmer typically consists of one or more microprocessors and contains programmable memory capable of storing executable programs under the control of the operator via a user interface. The implantable medical device may receive command instructions from the programmer. Such command instructions are referred to herein as "downlink transmissions", i.e., transmissions from the external device to the implanted medical device. In one example, the received command instructions may include program instructions or steps for directing the operation of the implantable medical device or may also include data such as program limits and timing data.

Similarly, the implanted medical device may transmit data to the external device (e.g., programmer unit) and the transmissions are referred to herein as "uplink" transmissions. The programmer may function to receive data from the implanted medical device as well as to transmit the commands to the implanted device. Communication between the implanted device and the external device may be limited to one-way transmissions or alternatively may include two-way transmissions. The communication between the implanted medical device and the external device is facilitated by corresponding receiving and transmitting circuitry included within the implanted medical device and the external device. Both the implanted medical device and the external device include antenna structures coupled to the receiver and transmitter-circuitry for transmitting and receiving electromagnetic energy.

Conventional telemetry systems typically enclose the antenna or antennas of the implanted medical device inside the housing or case of the implanted device. Such housings are typically metallic in nature and may be made of titanium or titanium alloys. The metal housings may act as low pass filters to limit the bandwidth of signals transmitted from and received by the implanted medical devices. In addition, telemetry systems that have antennas enclosed in the housing generally have undesirably low transmission rates.

With respect to conducting actual telemetric communications with implanted devices, it is preferable to use the near H field from the coil antenna rather than the E field. This is because the H field wave impedance is much less than the E field wave impedance, thereby allowing lower loss signal transmission through the metal housing and through the patient's skin (the near field is generally considered to be less than 1/6th of the wave length of the carrier wave). Therefore, uplink telemetry range depends upon the near field magnetic field strength or amplitude. The magnetic field strength, in turn, depends on the number of coil turns in the antenna, the area of the coil, and the coil current. The uplink transmitter efficiency depends on the coil quality factor"Q". To increase the telemetry uplink range, the magnetic field intensity must be maintained at an increased distance from the implanted device. The magnetic field may be increased by: adding more turns to the coil; making the coil antenna larger in area, winding it with a larger radius or by driving the coil with a larger coil current. The larger the coil Q, the more efficient the uplink transmitter circuit becomes. It should be noted that, for either uplink or downlink, it would be desirable to utilize only near-field magnetic fields (H fields), which do not require federal licensing since their amplitude falls off rapidly with link range.

Existing telemetry or equivalent systems rely on programming heads that must be precisely placed and positioned on the patient's IMDs (implanted medical devices) in order to transmit data. This is because the antenna is disposed in the moveable programmer head and the antenna must be placed in close proximity to the implantation site to effect agreeable data transmission link. The inability of the physician to see the IMD makes it even more difficult to establish the data link while the reliability of the data link is highly dependent on the signal strength that is obtained by proper: programming head orientation. A further complicating factor involves the physician handling the programming head while performing other important tasks. Constant repositioning of the programming head in order to maximize received signal strength makes completing the, telemetry functions undesirably difficult. Finally, establishing the telemetry in the exact location for a patient or a healthcare practitioner may be difficult if they have limited dexterity or if they need to hold the programming head in one position for extended periods of time.

SUMMARY OF THE INVENTION

Various embodiments of the present invention are directed to addressing the above and other needs in connection with providing a reliable, economical and non-invasive system for conveniently and chronically collecting cardiac and other IMD (implantable medical device) data. According to one aspect of the invention, collecting IMD data is simplified in order to promptly initiate, modify or control therapy and diagnosis in connection with chronic patient monitoring. In an example embodiment, a component of a telemetry or equivalent communications system includes a wearable article such as a vest, a wrist attachment or similar apparel or accessory that facilitates communication with an IMD to exchange clinical information from the IMD in the patient.

According to one embodiment of the invention, a telemetry arrangement for communicatively coupling an implanted medical device with a medical communications system has been discovered. The telemetry arrangement includes an article configured and arranged to be physically coupled to and donned on a body. The arrangement further includes an antenna member located on the article and configured and arranged to establish a communications link between the implanted device and the medical communications system.

According to another embodiment of the invention, a method and a system of establishing a telemetric communications link between an implantable device and a medical information communications system includes donning an article having an antenna member located thereon. A data communications link is then established between the implantable device and the medical communications system wherein a portion of the communications link is physically coupled to a body.

The above summary of the present invention is not intended to describe each illustrated embodiment or every implementation of the present invention. The figures in the detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
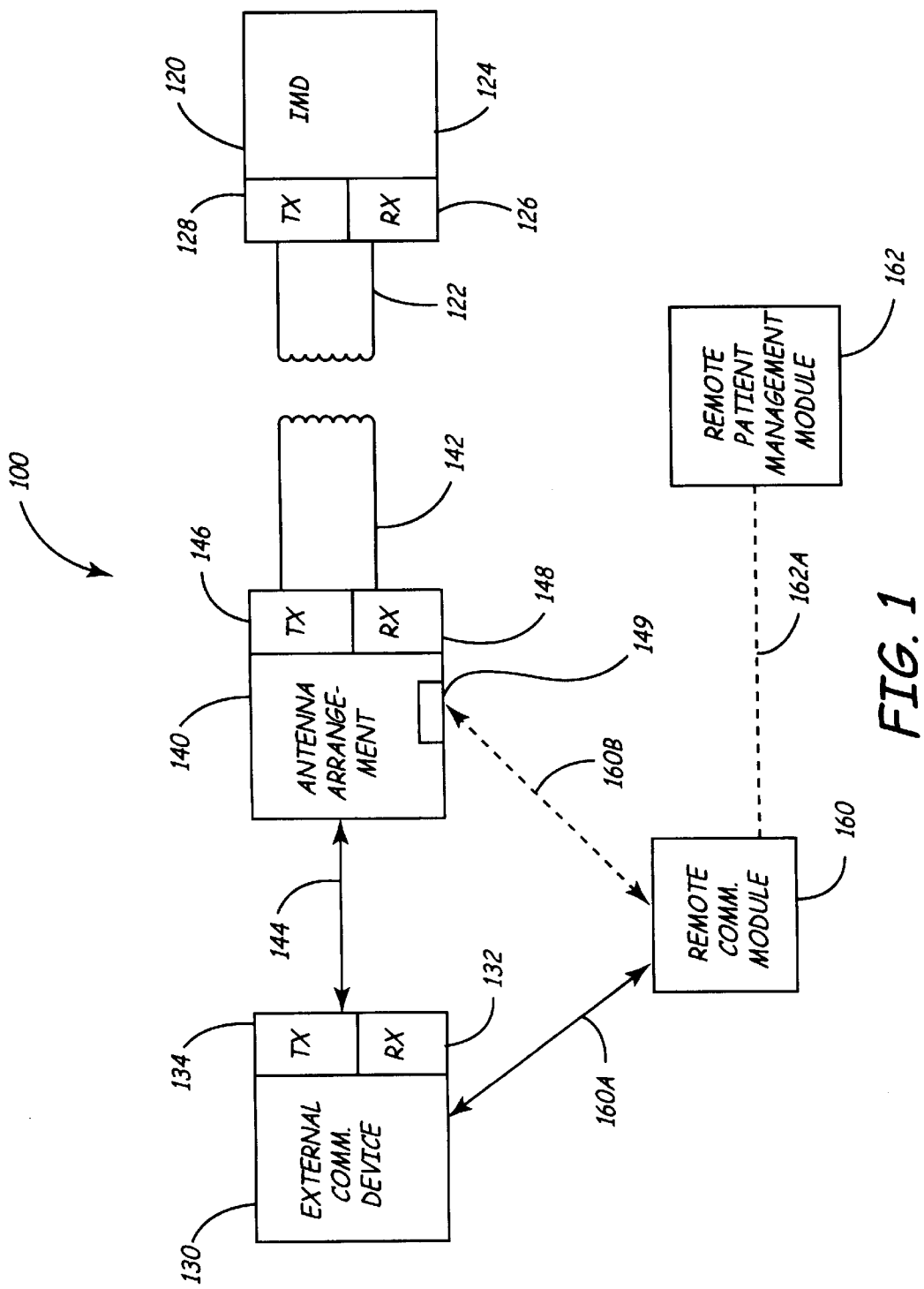
FIG. 1 illustrates a block diagram of a telemetry medical system for communicatively coupling an implantable medical device with a medical information communication system in accordance with an example embodiment of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is generally directed to a telemetry system and method for establishing a data link between an implanted device and an external medical, communications device. While the present invention is not necessarily limited to such an application, the invention will be better appreciated using a discussion of example embodiments in such a specific context.

In an example embodiment, the telemetry system is an integration of external monitors with IMDs to enable a continuous and reliable data feedback of physiological measurements upon which the therapeutic, diagnostic responses and operations of the IMD are based. In this regard the invention enables a closed-loop system that is structured to provide real-time continuous feedback to the IMD and medical care provider.

Referring now to the figures, FIG. 1 illustrates a block diagram of an implantable medical device telemetry system 100 that includes an implantable medical device 120, an external medical communications system 130 and an RF antenna arrangement 140 communicatively coupled to communications system 130. In this example embodiment, medical communications system 130 is a programming device capable of downloading information to implanted device 120 or uploading information from implanted device 120. Implanted device 120 and medical communications system 130 communicate via an inductive link provided by a first antenna 122 and RF antenna arrangement 140 that includes an antenna member 142. Antenna arrangement 140 is communicatively coupled to communications system 130 via a communications link 144. Communications link 144 can include a cabling system, an RF wireless link, an infrared link, an optical link or any other means that permits one or two way communications between arrangement 140 and system 130. When antenna member 142 of RF arrangement 140 is brought into proximity with the implanted device antenna 122, a current flow through either antenna 122 or antenna member 142 causes an inductive current in the corresponding antenna 122 or 142.

In this example, implanted device 120 is a cardiac pacemaker, and RF arrangement 140 operates much like a programming head device used by a physician to place, in close proximity to and to communicate with, the pacemaker. Implanted device 120 includes a housing 124, typically made of titanium or a titanium alloy, having a receiver 126 and a transmitter 128 that are electrically coupled-through a coupling network to antenna 122. A typical up-link telemetry path (information transmitted from the implanted device to the external communications system) begins with a request by RF antenna arrangement 140 for information from implanted device 120. In response, implanted device 120 enables transmitter 128 to transmit data through antenna 122 by inducing a current in antenna member 142. Information is then transmitted from antenna member 142 to a receiver 132 of communications system 130 via link 144, thereby completing the telemetry path.

In a related embodiment, telemetry system 100 includes a remote communications module 160 that provides a communications link to networks outside the immediate location of external medical communications system 130. For instance, module 160 provides a communications link to a telecommunications network, via a cellular link or hardwire connection, or a link to the Internet (World Wide Web) via a PC network or a wireless link to a global satellite communications network. The remote communications module would be coupled to medical communications system 130 via a remote communications link 160A, which can be hardwired or can be performed wirelessly.

In another related embodiment, all of the telemetry electronics from medical communications system 130 can be integrated with RF arrangement 140 in a telemetry electronics module 149, thereby providing greater mobility of RF arrangement 140. In another embodiment, RF arrangement 140 includes a module 149 that establishes a link via 160B with a remote communications module 160 to transmit/receive information over various communications networks including remote patient management modules 162 having a link via 162A. These remote patient management modules may include a web-enabled system that would supplement a doctor's care through device-specific education and tools for self-monitoring, immediate feedback or continuous health coaching and management for chronic patients.

In the context of cooperating with the remote patient management systems described in the patent applications listed above, various embodiments described herein enable a bi-directional communications system between the wearable telemetry system and a remote expert or doctor station. In one example application, the telemetry system or similar equivalent wireless system is structured to transmit the IMD data to a programming device and ultimately to a data center. At the data center, a healthcare specialist provides remote analysis of the IMD data and approves changes in therapy or diagnosis from the information received via the telemetry wearable article. Yet another embodiment of the present invention contemplates the use of one or more telemetry wearable articles for communicating with various IMDs implanted in the patient for various diagnostic and therapeutic activities. In a related application, external medical devices are programmed to continuously transfer data to an expert data center as well to the IMD(s). In yet another embodiment, the telemetry wearable articles are equipped with warning alarm systems to notify the patient and the remote physician about critical developments or impending problems based on anomalies in the readings or other physiological data trends.

Figure 2:
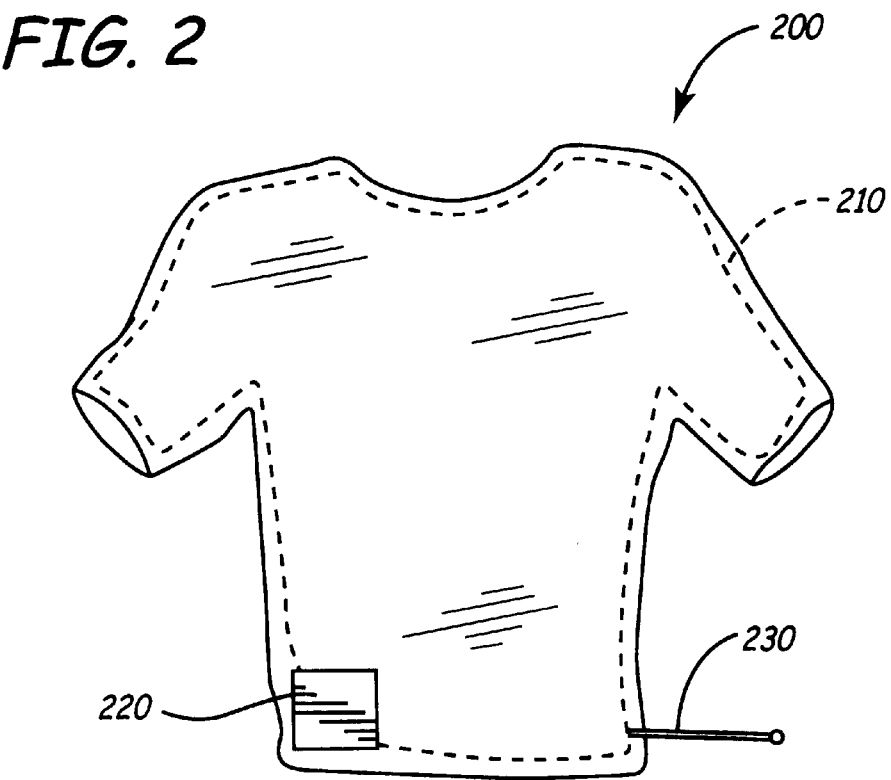
FIG. 2 illustrates an article with an antenna member thereon configured and arranged to be donned on a body in accordance with an example embodiment of the invention.

Referring now to FIG. 2, an example embodiment of RF antenna arrangement 140, in the form of a wearable article 200, establishes a data transmission link between implanted device 120 and medical communications system 130 of FIG. 1. Wearable article 200 includes a telemetry vest, for example, a shirt or similar type of vestment or apparel that includes an antenna member. In this example, the antenna member is in the form of a telemetry antenna band 210, disposed along the perimeter of the vestment that couples the medical communications system with antenna 122 of implanted device 120. Antenna band 210, coupled with the programming device, aids in providing a continuous real-time accurate measurement of clinically significant information collected from the implanted device (or various other IMDs) located in the patient.

Prior to implanted device 120 screening, the patient places telemetry vest 200 over the torso. Telemetry vest 200 is coupled to medical communications system 130, either via a hardwired cabling system or wirelessly (e.g., RF, infrared or optical). Medical communications system 130 then engages implanted device 120 through inductive coupling with antenna band 210 of telemetry vest 200. Once antenna 122 and antenna band 210 are inductively coupled, one or two way communications can take place between implanted device 120 and communications system 130. In an example application, telemetry vest 200 is formed with at least a pair of ECG (electrocardiogram) electrodes and with a telemetry electronics module 220. The telemetry electronics module (or circuit) 220 can include part or all of the components of the medical communication device thereby providing more mobility for the patient. In another example embodiment, antenna band 210 may be formed in such a manner to provide mobility of the antenna band within vest 200 to improve the proximity placement of the antenna band to implanted device 120. In yet another example application, telemetry vest 200 includes a telescoping antenna 230 that is coupled to module 220 for wireless communication to a remote data center or a remote medical communications system 130.

In an example embodiment, the wearable article has integrated electrodes for monitoring cardiac signals. A wearable article, configured and arranged to be physically coupled to and donned on the body, includes at least one pair of ECG electrodes disposed on the article that are configured and arranged to sense cardiac signals from a patient's heart. Where the wearable article is a vest, electrocardiograms can be easily conducted when the vest is donned by the patient. The ECG electrodes can be quickly and effortlessly placed proximate the patient's heart. The ECG electrodes are coupled to the medical information communications system either by cable or via a wireless circuit arrangement. A printing device is coupled to the medical information communication system to provide an ECG chart for the patient.

In another embodiment, the wearable vest includes an antenna member that is adapted to establish a communications link with a patient's implanted device. The antenna member is coupled to the medical information communications system either by cable or a wireless connection. A circuit module is coupled to the antenna member and located on the vest to provide wireless communication capabilities.

Figure 3:
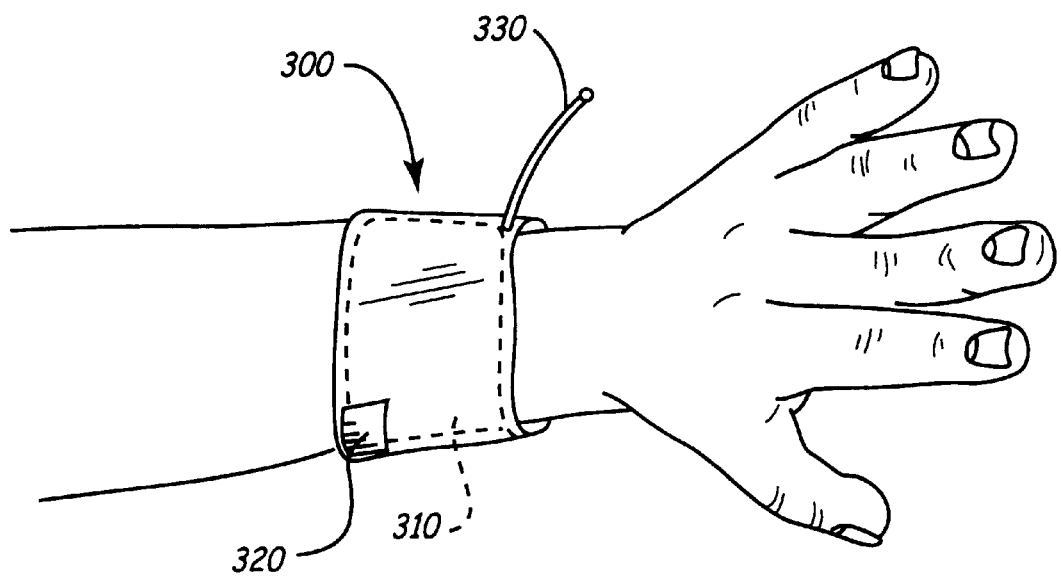
FIG. 3 illustrates another article with an antenna member thereon configured and arranged to be donned on a body in accordance with another example embodiment of the invention.

Referring now to FIG. 3, another example embodiment of an RF antenna arrangement in the form of a wristband or wrist attachment 300 is illustrated. Wristband 300 aids in establishing the data link between the external medical system 130 and the implanted device 120. The antenna member is in the form of a telemetry antenna band 310 and is disposed along the perimeter of the wristband. Antenna band 310 couples the medical communications system 130 with antenna 122 of implanted device 120 to provide a one or two way real time communications link with the implanted device (or various other IMFDs) located in the patient.

Prior to implanted device 120 screening, the patient places telemetry wristband 300 over the wrist. Telemetry wrist band 300 is coupled to medical communications system 130, either via a hardwired cabling system or wirelessly through a telescoping antenna 330 (or other forms of wireless communication as indicated earlier). Medical communications system 130 then engages implanted device 120 through inductive coupling with antenna band 310 of telemetry wristband 300, similarly as described with respect to the telemetry vest 200. In an example application, telemetry wristband 300 is coupled to a wearable telemetry electronics module 320 or an, electronics module that can be hardwired (or coupled wirelessly) to the wristband and then worn. The telemetry electronics module 320 has similar functionality to module 220 described above. In another example embodiment, telemetry wristband 300 includes a telescoping antenna 330 that is coupled to module 320 for wireless communication to a remote data center or a remote medical communications system 130. Telemetry module 320 and 220 in a related application can include the receiver and transmitter modules of communications system 130.

In an example embodiment, the wristband includes an antenna member that is adapted to establish a communications link with a patient's implanted device. The antenna member is coupled to the medical information communications system either by cable or a wireless connection. A circuit module is coupled to the antenna member and located on the wristband to provide the wireless communication capabilities.

Other wearable articles, or articles that can be donned on the body of the patient, that house an antenna band include, but are not limited to, a belt, a patch that adheres to a patient, a sheet that lays on a patient, a portable module and an article of jewelry. The communications link is also established where these articles are draped on the body of the patient, such as where the antenna member is located on a sheet member.

In a related application, the communications link with the implanted device is established with an article that is attached to an article of apparel such that the antenna member is in close proximity to the patient's body. The article having the antenna member can be attached to the shirt or top of the patient or removably attached to the belt or other article of clothing.

In another related embodiment, telemetry system 100 can couple with an implanted device 120 where device 120 uses the body as an antenna and is described in U.S. Ser. No. 09/218,946, now U.S. Pat. No. 6,115,636 to Ryan, and is incorporated by reference in its entirety. Since RF arrangement 140 would be positioned in the near-field communications volume 20 by using, for example, the vest or wrist band embodiments, a communications link is established between the external communication device 130 and implanted device 120.

Some of the advantages provided by the various embodiments of the present invention include increased flexibility of patient, movement while improving programmer proximity placement about the implant site without corrupting the data transferred; and increased accuracy of data being communicated between the implanted device and the external medical device. In addition, the present invention provides for a comfortable distance between patient and clinician or physician when performing telemetry and eliminates the necessity of a lengthy time period in which the programmer must be held in a particular position to accomplish adequate and accurate communication.

Figure 4:
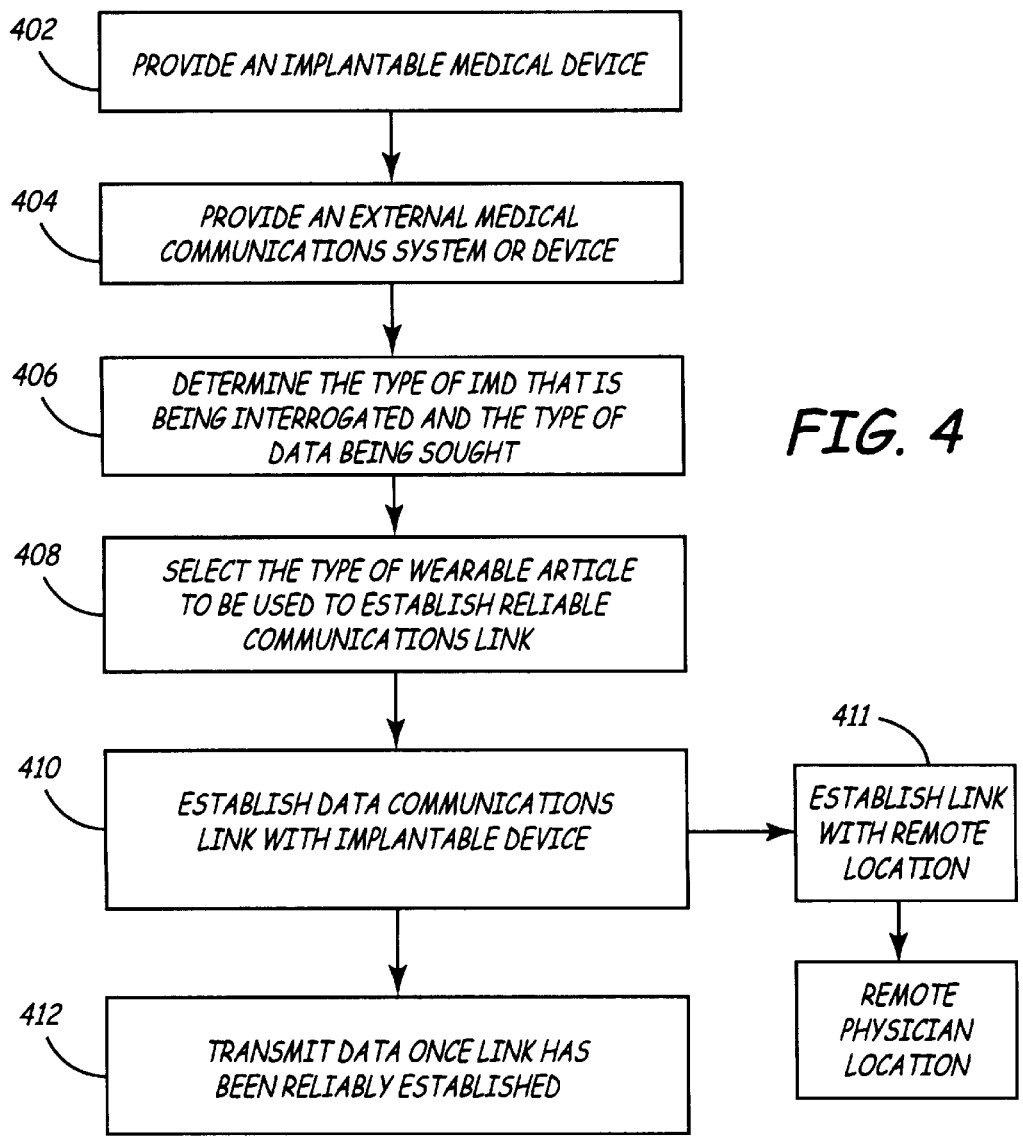
FIG. 4 is a flowchart illustrating the manner of coupling the implantable medical device with the medical communications system via the antenna member of the article in accordance with an example embodiment of the invention.

Referring now to FIG. 4, flowchart 400 illustrates the manner of establishing a telemetric communications link between an implanted medical device and an external medical communications system or device via a wearable RF antenna arrangement (hereinafter wearable article). At 402, an implanted medical device is provided that is configured and arranged to communicate with an external medical communications system. At 404, an external medical communications system external to the body is provided that is configured and arranged to communicate with the implantable device. At 406, a determination is made of the type of implanted device that is within the patient (e.g. pacemaker, defibrillator, etc.) for purposes of initiating the proper level of communication. At 408, a determination is made of the type of wearable article to be used that will be most effective in establishing a reliable communications link with the implanted device. At 410, a data communications link is established between the external medical communications system and the implanted medical device via the selected wearable article. Depending on where the physician is located, a remote communications link may need to be established at 411 before any transmission of data occurs with the implanted device. Once the data link is established and reliability is assured, uplink or downlink communications can commence at 412.

The present inventions provides, in an example application, non-invasive clinical data measurements for (or control of) various IMDs including but not limited to drug pumps, neurological implants, nerve stimulators, various cardiac implants and equivalent medical devices. The present invention is compatible to a number of techniques for interrogating implanted medical devices. In addition, embodiments described are compatible with remote patient management: systems that interact with remote data and expert data centers and compatible with a data communication system that enables the transfer of clinical data from the patient to a remote location for evaluation, analysis, data reposition and clinical evaluation. Other communications systems can be integrated into the present invention including wireless, microwave and global satellite communications.

Various modifications, equivalent processes, as well as numerous structures to which the present invention may be applicable will be readily apparent to those of skill in the art to which the present invention is directed upon review of the present specification. The claims are intended to cover such modifications and devices.

We claim:

1. A telemetry arrangement for communicatively coupling an implanted medical device with a medical information communications system, the telemetry arrangement comprising:
    an article configured and arranged to be physically coupled to and donned on a body; and
    an antenna member disposed on the article and configured and arranged to establish a communications link between the implanted device and the medical communications system;
    a pair of ECG electrodes disposed on the article in an arrangement to sense cardiac signals from a patient's heart; and
    means for coupling the ECG electrodes to the medical communications system.

2. The telemetry arrangement of claim 1, wherein the telemetry arrangement further includes a circuit module disposed on the article and coupled to the antenna member configured and arranged to communicate with the medical information communications system.

3. The telemetry arrangement of claim 2, wherein the circuit module includes a receiver module coupled to the antenna member configured and arranged to provide an uplink data transmission link between the implanted device and the medical communications system.

4. The telemetry arrangement of claim 3, including a vest that is electrically coupled to the receiver module.

5. The telemetry arrangement of claim 2, wherein the circuit module includes a transmitter module coupled to the antenna member configured and arranged to provide a downlink data transmission link between the implanted device and the medical communications system.

6. The telemetry arrangement of claim 5, wherein the circuit module includes a receiver module coupled to the antenna member configured and arranged to provide an uplink data transmission link between the implanted device and the medical communications system.

7. The telemetry arrangement of claim 2, wherein the circuit module includes means for providing an alert advising of a problem with the implanted medical device.

8. The telemetry arrangement of claim 1, wherein the circuit module includes a telemetry circuit coupled to the ECG electrodes.

9. The telemetry arrangement of claim 3, wherein the article is a wearable vest having the antenna member disposed on a perimeter of the vest.

10. The telemetry arrangement of claim 1, wherein the implanted medical device is one of the group consisting of: pacemakers, drug pumps, neurological implants, nerve stimulators and cardiac implants.

11. The telemetry arrangement of claim 1, wherein the article is a vest having the antenna member disposed on a perimeter of the vest.

12. A telemetry arrangement for communicatively coupling an implanted medical device with a medical information communications system, the telemetry arrangement comprising:
    an article configured and arranged to be physically coupled to and donned on a body;
    an antenna member disposed on the article and configured and arranged to establish a communications link between the implanted device and the medical communications system; and
    a telescoping antenna coupled to the antenna member.

13. A telemetry arrangement for communicatively coupling an implanted medical device with a medical information communications system, the telemetry arrangement comprising:
    an article configured and arranged to be physically coupled to and donned on a body;
    an antenna member disposed on the article and configured and arranged to establish a communications link between the implanted device and the medical communications system; and
    wherein the article is a wrist attachment having the antenna member disposed on a perimeter of the wrist attachment.

14. The telemetry arrangement of claim 13, wherein the wrist attachment further includes a telescoping antenna coupled to the antenna member.

15. A telemetry arrangement for communicatively coupling an implanted medical device with a medical information communications system, the telemetry arrangement comprising:

an article configured and arranged to be physically coupled to and donned on a body;

an antenna member disposed on the article and configured and arranged to establish a communications link between the implanted device and the medical communications system; and a circuit module disposed on the article and coupled to the antenna member configured and arranged to communicate with the medical information communications system; the circuit module including:

(i) a transmitter module coupled to the antenna member configured and arranged to provide a downlink data transmission link between the implanted device and the medical communications system;

(ii) a receiver module coupled to the antenna member configured and arranged to provide an uplink data transmission link between the implanted device and the medical communications system; and wherein the circuit module is configured and arranged to establish two way communication of data between the implanted medical device and the medical communications system via a communications network selected from the group consisting of: wireless, microwave and global satellite communications.

16. A telemetry arrangement for communicatively coupling an implanted medical device with a medical information communications system, the telemetry arrangement comprising:

an article configured and arranged to be physically coupled to and donned on a body;

an antenna member disposed on the article and configured and arranged to establish a communications link between the implanted device and the medical communications system; and a circuit module disposed on the article and coupled to the antenna member configured and arranged to communicate with the medical information communications system; the circuit module including:

(i) a transmitter module coupled to the antenna member configured and arranged to provide a downlink data transmission link between the implanted device and the medical communications system;

(ii) a receiver module coupled to the antenna member configured and arranged to provide an uplink data transmission link between the implanted device and the medical communications system; and wherein the circuit module is configured and arranged to establish two way communication of data between the implanted medical device and the medical communications system via the Internet, a LAN, a WAN, a local network and a public service telephone network.

17. A telemetry arrangement for communicatively coupling an implanted medical device with a medical information communications system, the telemetry arrangement comprising:

an article configured and arranged to be physically coupled to and donned on a body;

an antenna member disposed on the article and configured and arranged to establish a communications link between the implanted device and the medical communications system; and a circuit module disposed on the article and coupled to the antenna member configured and arranged to communicate with the medical information communications system; and wherein the circuit module is arranged and configured to provide a data link to a plurality of implanted medical devices.

18. A telemetry arrangement for communicatively coupling an implanted medical device with a medical information communications system, the telemetry arrangement comprising:

an article configured and arranged to be physically coupled to and donned on a body;

an antenna member disposed on the article and configured and arranged to establish a communications link between the implanted device and the medical communications system; and a circuit module disposed on the article and coupled to the antenna member configured and arranged to communicate with the medical information communications system; and wherein the article further includes a plurality of circuit modules located therein for providing communication links to a plurality of implanted devices.

19. A method for establishing a telemetric communications link between an implanted medical device in a body and a medical information communications system, the method comprising:

donning an article of apparel with an antenna member located thereon; and establishing a data communications link between the implanted medical device and the medical communications system via the antenna member and the body;

wherein the step of donning the article includes the step of donning one of the articles from the group consisting of: a shirt, a vest, a belt, an article of jewelry, and an accessory; and wherein the step of selecting the article includes providing a telescoping antenna coupled to the antenna member.

20. The method of claim 19, wherein the step of establishing the communications link further includes the steps of:

determining the type of implanted medical device with which the telemetric communications link is being sought; and selecting the article that places the antenna member thereon in close proximity to implanted device.

21. A method for establishing a telemetric communications link between an implanted medical device in a body and a medical information communications system, the method comprising:

donning an article of apparel with an antenna member located thereon; and establishing a data communications link between the implanted medical device and the medical communications system via the antenna member and the body; and wherein the step of establishing a data communications link further includes the step of providing a plurality of articles and antenna members located thereon for establishing data links to a plurality of implanted medical devices.

22. The method of claim 21, wherein the step of donning the article includes draping the article on the body.

23. A system for establishing a telemetric communications link between an implanted medical device and a medical information communications system, the system comprising:
  an article to be donned on a patient's body;
  means for establishing a data communications link between the implanted medical device and the medical communications system;
  a pair of ECG electrodes disposed on the article in an arrangement to sense cardiac signals from a patient's heart; and
  means for coupling the ECG electrodes to the medical communications system.

24. The system of claim 23, wherein the article further includes a circuit module located thereon and coupled to the antenna member configured and arranged to communicate with the medical information communications system.

25. The system of claim 24, wherein the circuit module includes a telemetry circuit coupled to the ECG electrodes.

26. The system of claim 24, wherein the circuit module includes a receiver module coupled to the antenna member configured and arranged to provide an uplink data transmission link between the implanted device and the medical communications system.

27. The system of claim 24, wherein the circuit module includes a transmitter module coupled to the antenna member for providing a downlink data transmission link between the implanted device and the medical communications system.

28. The system of claim 24, wherein the circuit module includes a receiver module coupled to the antenna member configured and arranged to provide an uplink data transmission link between the implanted device and the medical communications system.

29. The system of claim 24, wherein the circuit module further includes means for providing an alert advising of a problem with the implanted medical device.

30. The system of claim 28, wherein the article is a vest having the antenna member disposed on a perimeter of the vest.

31. The system of claim 23, wherein the implanted medical device is one of the group consisting of: pacemakers, drug pumps, neurological implants, nerve stimulators and cardiac implants.

32. A system for establishing a telemetric communications link between an implanted medical device and a medical information communications system, the system comprising:
  an article with an antenna member;
  means for establishing a data communications link between the implanted medical device and the medical communications system via the antenna member; and
  wherein the article is a wrist attachment having the antenna member disposed on a perimeter of the wrist attachment.

33. The system of claim 32 wherein the wrist attachment further includes a telescoping antenna coupled to the antenna member.

34. A system for establishing a telemetric communications link between an implanted medical device and a medical information communications system, the system comprising:
  an article with an antenna member;
  means for establishing a data communications link between the implanted medical device and the medical communications system via the antenna member and the body;
  wherein the article further includes a circuit module located thereon and coupled to the antenna member configured and arranged to communicate with the medical information communications system; and
  wherein the circuit module is configured and arranged to establish two way wireless communication of data between the implanted medical device and the medical communications system.

35. The system of claim 34, wherein the circuit module is configured and arranged to establish two way communication of data between the implanted medical device and the medical communications system via a communications network selected from the group consisting of: wireless, microwave and global satellite communications.

36. A system for establishing a telemetric communications link between one or more implanted medical device and a medical information communications system, the system comprising:
  an article with an antenna member;
  means for establishing a data communications link between the implanted medical device and the medical communications system via the antenna member and the body;
  wherein the article further includes a circuit module located thereon and coupled to the antenna member configured and arranged to communicate with the medical information communications system; and
  wherein the circuit module is arranged and configured to provide a data link to a plurality of implanted medical devices.

37. A system for establishing a telemetric communications link between an implanted medical device and a medical information communications system, the system comprising:
  an article with an antenna member;
  means for establishing a data communications link between the implanted medical device and the medical communications system via the antenna member and the body; and
  wherein the article further includes a plurality of circuit modules located thereon configured and arranged to provide communication links to a plurality of implanted devices.

38. An arrangement for monitoring cardiac signals, the monitoring arrangement comprising:
  an article configured and arranged to be physically coupled to and donned on a body; and
  at least one pair of ECG electrodes located on the article and configured and arranged to sense cardiac signals.

39. The arrangement of claim 38, wherein the article is a vest having the ECG electrodes integrated therein in a position that is proximate a patient's heart when the vest is donned.

40. The arrangement of claim 39, further including a circuit module coupled to the ECG electrodes, wherein the circuit module is configured and arranged to communicate with a medical information communications system.

41. The arrangement of claim 40, further including an antenna member located on the vest and communicatively coupled to the medical communications system.

42. The arrangement of claim 40, wherein the circuit module includes a telemetry circuit configured and arranged to provide wireless communication with the medical information communications system.

43. An arrangement for establishing a communication link with an implanted medical device, the arrangement comprising:

an article of apparel configured and arranged to be physically coupled to and donned on a body;

an antenna member disposed on the article and configured and arranged to establish the communications link with the implanted device; and a circuit module disposed on the article and coupled to the antenna member configured and arranged to communicate with a medical information communications system; and wherein the article is a wristband attachment having the antenna member disposed thereon.

44. The arrangement of claim 43, wherein the circuit module includes a telemetry circuit configured and arranged to provide wireless communication with the medical information communications system.

* * * * *